US012685845B2

(12) United States Patent
Righini

(10) Patent No.: US 12,685,845 B2
(45) Date of Patent: Jul. 21, 2026

(54) DEVICE FOR CAPTURING GUIDE WIRES

(71) Applicant: INNOVHEART S.r.l., Milan (IT)

(72) Inventor: Giovanni Righini, Gland (CH)

(73) Assignee: INNOVHEART S.r.l., Milan, MI (US)

( * ) Notice: Subject to any disclaimer, the term of this patent is extended or adjusted under 35 U.S.C. 154(b) by 849 days.

(21) Appl. No.: 17/999,116

(22) PCT Filed: May 26, 2021

(86) PCT No.: PCT/IB2021/054571
§ 371 (c)(1),
(2) Date: Nov. 17, 2022

(87) PCT Pub. No.: WO2021/240381
PCT Pub. Date: Dec. 2, 2021

(65) Prior Publication Data
US 2023/0211129 A1 Jul. 6, 2023

(30) Foreign Application Priority Data
May 27, 2020 (IT) ......................... 102020000012625

(51) Int. Cl.
*A61M 25/09* (2006.01)

(52) U.S. Cl.
CPC ... *A61M 25/09* (2013.01); *A61M 2025/09116* (2013.01); *A61M 2025/09166* (2013.01)

(58) Field of Classification Search
CPC .......... A61B 2017/00358; A61B 2017/22035; A61B 17/221; A61B 17/00234; A61B 2017/22038; A61B 2017/2212; A61B 2017/2217; A61B 2090/3966; A61B 17/0057; A61B 18/1492; A61B 2017/00915; A61B 2017/00924;
(Continued)

(56) References Cited

U.S. PATENT DOCUMENTS 6,458,145 B1    10/2002   Ravenscroft et al.
2008/0086149 A1   4/2008   Diamant et al.
(Continued)

FOREIGN PATENT DOCUMENTS

EP      2489313 A1 *   8/2012   ............. A61B 17/50
EP      2922501 B1     9/2015

OTHER PUBLICATIONS

International Search Report issued in corresponding International Application No. PCT/IB2021/054571, date of mailing Sep. 24, 2021 (5 pages).
(Continued)

*Primary Examiner* — Katherine M Shi
(74) *Attorney, Agent, or Firm* — FLYNN THIEL, P.C.

(57) ABSTRACT

A device (10) for capturing a guide wire (50) comprises a snaring device (20, 30) and an auxiliary catheter (40). The auxiliary catheter (40) is configured to slidingly accommodate the guide wire to be caught so as to extend a distal end (47) thereof beyond the distal end of the guide wire in order to be caught by the snaring device (20, 30) while the guide wire (50) is in a retracted position in the auxiliary catheter (40). The auxiliary catheter preferably comprises a portion which is at least partially echo-transparent and/or radio-transparent and an end portion (44) which is radio-opaque and/or echo-opaque.

8 Claims, 1 Drawing Sheet

(58) Field of Classification Search
CPC .. A61B 2090/3925; A61B 2017/00292; A61B
90/39; A61M 2025/09116; A61M 25/09;
A61M 2025/09166
See application file for complete search history.

(56) References Cited

U.S. PATENT DOCUMENTS

| | | | |
|---|---|---|---|
| 2012/0029526 A1 | 2/2012 | Hewitt et al. | |
| 2015/0245910 A1* | 9/2015 | Righini | A61F 2/2436 |
| | | | 623/2.11 |
| 2018/0325505 A1* | 11/2018 | Phillips | A61B 17/0057 |

OTHER PUBLICATIONS

Written Opinion of the International Searching Authority issued in corresponding International Application No. PCT/IB2021/054571, date of mailing Sep. 24, 2021 (7 pages).

* cited by examiner

DEVICE FOR CAPTURING GUIDE WIRES

FIELD OF THE INVENTION

The present invention relates to a device for capturing guide wires. In particular, it relates to a device for capturing an end of a guide wire which is inserted in a patient and for bringing it outside the patient him/herself.

The invention has been developed with particular regard, though in a non-limiting manner, to a snaring device for guide wires which is particularly advantageous for arranging a guide wire around an anatomical structure during a transcatheter surgical procedure. For example, there is the need for a device which is suitable for arranging a guide wire for guiding the implantation of a prosthesis for a heart valve in order to replace the physiological function of a malfunctioning heart valve.

TECHNOLOGICAL BACKGROUND

It is known to use guide wires during intervention procedures of low invasiveness, called transcatheter procedures. Such procedures afford access to the desired position, for example, though not exclusively, inside the heart, by navigating inside the vascular system. The guide wires which are correctly positioned are then used to guide the insertion of various devices, for example, vascular stents or heart valves prostheses.

Sometimes, a percutaneous therapeutic procedure or a low invasiveness procedure requires that an end of a guide wire be caught in order to bring it outside the patient. For example, this necessity is present when it is desirable to use a guide wire in order to surround an anatomical structure. The Applicant has particularly encountered this necessity when arranging a guide wire around the anatomical structure of a heart valve in order to be able to subsequently guide the insertion of a component of a valve prosthesis which encloses from the exterior the native leaflets of the valve which is subjected to the therapy.

To this end, there have been known for some time snaring devices for guide wires, which are typically formed by a plurality of loops which are grouped together. A device of this type, which is known as a snaring device, is positioned in such a manner that the guide wire to be captured crosses at least one of the loops. It is then withdrawn inside a catheter so as to capture the guide wire which, folded near the end thereof, is drawn into the same catheter.

A problem of the devices of the known type is that they irreparably damage the guide wire; this is because the guide wire is normally made of metal, for example steel, and, when it is grasped by the snaring device, with a mechanical action which is very concentrated, and folded in order to be retrieved outside the patient, a permanent plastic deformation is brought about. Therefore, it is no longer possible to recover the geometry and the original functionality of the guide wire. In some cases, however, it is still necessary to use the folded end of the wire for subsequent operations, for example, in order to insert a device. The presence of a permanent deformation hinders or even prevents such subsequent operations.

STATEMENT OF INVENTION

An object of the invention is to solve the problems of the prior art. In particular, it is intended to provide a device for capturing an end of a guide wire without damaging it. Another object is to construct an economical, simple, reliable to use and safe device.

According to a first aspect, there is described a device for capturing a guide wire comprising a snaring device. The snaring device may comprise a snaring member, which may be accommodated inside a first catheter. The device for capturing a guide wire may comprise an auxiliary catheter or second catheter. The auxiliary catheter may be suitable for accommodating, during use, the guide wire which the device for capturing a guide wire is intended to capture. The device is suitable for capturing, during use, a guide wire without bending it. The auxiliary catheter may be configured to slidingly accommodate the guide wire to be caught so as to extend a distal end thereof beyond the distal end of the guide wire. The auxiliary catheter can be caught by the snaring device while the guide wire is in a retracted position in the auxiliary catheter.

According to another aspect, there is described a device for capturing a guide wire comprising an auxiliary catheter which may be at least partially echo-transparent and/or radio-transparent over at least a portion thereof. This at least partially echo-transparent and/or radio-transparent portion of the auxiliary catheter may be predominant. The mutual positioning between the guide wire and the second catheter is thereby allowed to be visible during use. The correct positioning of the guide wire is thereby made easier with respect to the snaring device when it is used in an operation with a percutaneous or low invasive procedure.

According to another aspect, the at least partially echo-transparent and/or radio-transparent portion of the auxiliary catheter is flexible. Preferably, it can be collapsed or folded without tearing or detaching from the remainder of the auxiliary catheter. In this manner, it can be caught and drawn by the snaring device without losing the continuity of the auxiliary catheter.

According to another aspect, a device for capturing a guide wire may comprise an auxiliary catheter which is provided with a radio-opaque and/or echo-opaque portion. The correct positioning thereof is thereby made easier when it is used in an intervention with a transcatheter procedure.

The radio-opaque and/or echo-opaque portion of the auxiliary catheter may be positioned near an end hole of the auxiliary catheter. The radio-opaque and/or echo-opaque portion may have such a length as to be able to be displayed in the folded form when the auxiliary catheter is caught and blocked between the snaring device and the end of the catheter of the snaring device and/or during the introduction of the auxiliary catheter into the catheter of the snaring device. For example, it may be at least 10 mm and more preferably at least 20 mm long.

The auxiliary catheter may be folded in the radio-opaque and/or echo-opaque portion or in the echo-transparent and/or radio-transparent portion. In particular, it can be folded so as to form an acute angle, with a radius of curvature which is small, for example, less than 1 mm.

According to another aspect, there is described a device for capturing a guide wire comprising a snaring device which may comprise a snaring member with at least one loop. The at least one loop may be mounted on a rod.

There is further described a device for capturing a guide wire comprising an auxiliary catheter which may have such an internal diameter as to allow the insertion and sliding of the guide wire only.

According to another aspect, there is described a device for capturing a guide wire comprising an auxiliary catheter which is suitable for accommodating, during use, the guide wire which the device for capturing a guide wire is intended to capture; the auxiliary catheter can be constructed from polymer material.

According to another aspect, there is also described a method for capturing a guide wire. The method may comprise the step of positioning the guide wire in a desired position; this operation may be carried out with a known method. The method may comprise the step of positioning a snaring device so that an end portion of the guide wire engages with it. Preferably, a snaring device may be positioned so that an end portion of the guide wire crosses at least one loop of a snaring member of the snaring device. The method may comprise the step of arranging an auxiliary catheter or second catheter along the guide wire. Preferably, the second catheter is provided in such a manner that an end portion of the guide wire extends out of a lumen of the second catheter, preferably from an end hole in which the lumen of the second catheter terminates. The method may comprise the step of causing the second catheter to slide over the guide wire so that it engages with the snaring device, for example, by crossing the at least one loop of the snaring member of the snaring device. The method may comprise the step of withdrawing the guide wire in such a manner that it does not engage with the snaring device, while remaining inside the second catheter. The method may comprise the step of withdrawing the snaring member of the snaring device inside a first catheter. It is thereby possible to capture the second catheter between the snaring device and the end of the first catheter and/or where applicable to also drag the second catheter inside the first catheter.

According to another aspect, the method may provide for the additional step of gently tightening the snaring device around the guide wire before the step of causing the second catheter to slide over the guide wire until also engaging with the snaring device. Advantageously, it is thereby possible to stabilize the position of the end of the guide wire but without damaging the structure thereof.

According to another aspect, the method may comprise the additional step of gently tightening the snaring device around the second catheter before the step of withdrawing the guide wire. Advantageously, the second catheter is thereby stabilized by means of the snaring device so as to maintain the position thereof.

According to a particular aspect, the method may provide for folding a radio-opaque or echo-opaque portion of the second catheter when the snaring member captures and blocks the second catheter against the end hole of the first catheter or when it drags it inside the first catheter, thereby indicating visually by means of echographic and/or radiographic images the correct capture of the second catheter by the snaring device.

BRIEF DESCRIPTION OF THE DRAWINGS

Additional features and advantages will become clear from the following detailed description of a preferred embodiment of the invention with reference to the appended drawings which are provided purely by way of non-limiting example and in which.

DETAILED DESCRIPTION

Figures 1, 2, 3, 4:
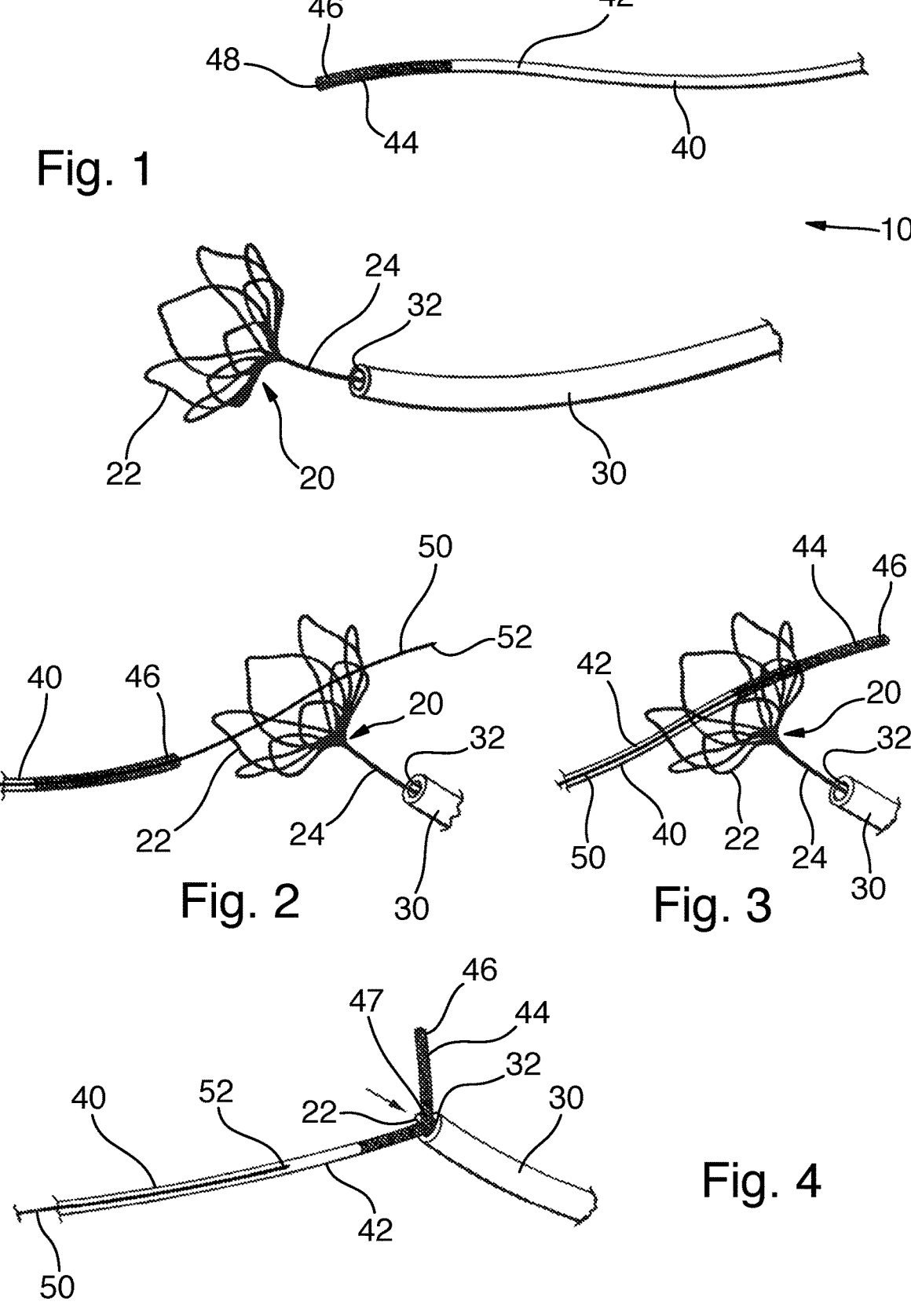
FIG. 1 illustrates a device for capturing a guide wire.
FIG. 2 illustrates the device of FIG. 1 during a first step of a method for capturing a guide wire.
FIG. 3 illustrates the device of FIG. 1 during a second step of a method for capturing a guide wire.
FIG. 4 illustrates the device of FIG. 1 during a third step of a method for capturing a guide wire.

With reference now to FIG. 1, a device 10 for capturing a guide wire comprises a snaring device which comprises a snaring member 20 which is accommodated inside a first catheter 30. The device 10 further comprises a second catheter 40.

The snaring member 20 may be of any type known in the field, such as a snaring device, with different geometries. In the preferred embodiment, which is depicted, the snaring member 20 comprises a plurality of loops 22. The loops 22 are mounted on a rod 24. The loops 22 can each be arranged with a different orientation, for example, so as to form a flower-like structure. This does not exclude an embodiment with a different snaring member 20, for example, formed even by a single loop 22 mounted on the rod 24. The first catheter 30 is preferably a catheter with a single lumen, in which the snaring member 20 can slide. The lumen of the catheter 30, that is to say, the longitudinal conduit which extends through it, ends in an end hole 32.

The second catheter 40 is a catheter for accommodating a guide wire 50, as can be seen, for example, in FIG. 2, in particular the guide wire intended to be caught by the device of the present invention. To this end, the second catheter 40 preferably has an internal diameter of the lumen sufficient to allow the insertion and the sliding of the guide wire 50 only. In other words, the second catheter 40 allows the guide wire 50 to be inserted with minimal play. The second catheter 40 is preferably constructed from a flexible material, for example, from elastomer material or other polymer material. In detail, the second catheter 40 has a thin wall of polymer material so as to be flexible. The second catheter 40 may thus readily be conformed to the path of the guide wire 50, above which it is intended to slide and can be folded freely without being subjected to any permanent deformation. Furthermore, the second catheter 40 is preferably at least partially echo-transparent and/or radio-transparent (that is to say, at least partially transparent with respect to echography and/or X-rays) in at least one portion thereof. Preferably, the at least partially echo-transparent and/or radio-transparent portion constitutes a predominant portion 42 of the second catheter 40. The second catheter 40 is further preferably provided with a radio-opaque and/or echo-opaque portion 44. This portion is preferably located at the distal end 46 of the second catheter near an end hole 48, for the outlet of the lumen thereof. Preferably, the radio-opaque and/or echo-opaque portion has a length greater than or equal to the width of one or more of the loops 22 of the snaring device 20. The radio-opaque and/or echo-opaque portion may have such a length as to be able to be displayed in folded form during the introduction of the second catheter 40 in the first catheter 30.

Preferably, therefore, the second catheter 40 has both an at least partially echo-transparent and/or radio-transparent portion, which is preferably a predominant portion, and a radio-opaque and/or echo-opaque portion, which is preferably located in the region of or near the end of the catheter.

With reference now to FIGS. 2, 3 and 4, there will be described the method for capturing an end of the guide wire 50 using the device 10 described above. In particular, the method allows the end of the guide wire inserted in a patient to be caught and allows it to be brought outside the patient without folding it or damaging it.

The guide wire 50 is positioned in the desired position. If it is desirable to position the guide wire with reference to an anatomical structure, for example, in order to completely or partially surround a heart valve, the positioning may be carried out by means of a system of catheters, including one with several stages, having, for example, ends which are or can be orientated, or in some other manner. When the guide wire 50 is in the desired position, the snaring device is positioned in such a manner that the end portion 52 of the guide wire 50 crosses or engages with at least one loop 22 of the snaring member 20, as can be seen in FIG. 2.

The method usually carried out at this point, according to the prior art in the sector of the percutaneous and/or trans-catheter methods, would involve withdrawal of the snaring member 20 inside the first catheter 30, drawing with it the guide wire 50 which is also folded inside the first catheter 30.

According to the invention, however, the method continues by putting the second catheter 40 on the guide wire 50, causing it to slide over it until the end of the second catheter reaches the end of the guide wire which is introduced or engaged in the snaring member 20. The second catheter 40 is thus also crossing at least one loop 22 of the snaring member 20, as can be seen in FIG. 3. The radio-opaque and/or echo-opaque portion 44 of the catheter 40 provides an auxiliary member for ensuring that the catheter 44 is in the desired position, in a state introduced in the snaring member 20 in a position suitable for the subsequent capture thereof. In fact, it is possible to verify that the radio-opaque and/or echo-opaque portion of the catheter 40 overlaps, in the image generated by echography or radiography, the merely radio-opaque or echo-opaque images of one or more loops 22 of the snaring member 20.

While maintaining the second catheter 40 in this position, where applicable by means of the snaring member 20 which is lightly caught around the second catheter 40, the guide wire 50 is withdrawn in such a manner that the end portion 52 thereof does not cross or engage with the loops 22 of the snaring device 20 any more. Using the echo-transparent and/or radio-transparent portion of the second catheter 40, it is possible to verify that the end of the guide wire 50 has been withdrawn sufficiently, leaving the radio-opaque and/or echo-opaque portion at the end of the second catheter 40.

The snaring member 20 is therefore withdrawn inside the first catheter 30 (FIG. 4). In this manner, it is possible to draw inside it the second catheter 40, too, which is folded in a folding zone 47. It may be noted that, as can be seen in FIG. 4, the guide wire 50 is not folded because the end portion 52 thereof has previously been withdrawn sufficiently in the second catheter 40 with respect to the end thereof and therefore is not in the folding zone 47.

In this step, the radio-opaque and/or echo-opaque portion 44 of the catheter 40 provides a fundamental help for ensuring the success of the withdrawal operation of the second catheter 40 inside the first catheter 30. By adequately configuring the extent of the radio-opaque or echo-opaque portion 44 in such a manner that the folding zone 47 falls therein, it is possible to verify the effective folding of the catheter 40 by means of echography and/or radiography. If, depicting the snaring member 20 inside the first catheter 30, the radio-opaque or echo-opaque end 44 of the second catheter 40 remains substantially stretched without being folded, the operator would have the prompt indication that the capture by the snaring member 20 has not been carried out and could therefore return to extract the snaring member 20 in order to repeat the preliminary operations indicated above. Otherwise, the display of the folding of the radio-opaque or echo-opaque end 44 would confirm the completed capture of the second catheter 40 by the snaring member 20 and would provide the permission to continue the planned operations, as described below.

In accordance with the diameters of the first and second catheters 30 and 40 used, it is possible to retract the second catheter 40 without drawing it inside the first catheter 30 but only by capturing it between the snaring member and the end hole 32 of the first catheter in the configuration shown in FIG. 4. It is therefore possible to retract together the first catheter 30 and the snaring member 20 in order to recover the distal end 46 of the second catheter 40 and the guide wire therewith.

At this point, the snaring device allows recovery at the exterior of the patient of the distal end of the second catheter 40 with the guide wire 50 therein. It is therefore possible to remove the second catheter 40 while leaving the single guide wire 50 in position.

The result of the method described above is the guide wire 50 is correctly positioned and with both the ends thereof, which are intact and non-deformed, accessible for the operator. It is thereby possible to also use the end portion 52 of the guide wire 50 to insert additional devices which have to slide "over the wire" or more generally to carry out any operation which requires the end portion 52 of the guide wire 50 not to become deformed or damaged.

As described above, the second catheter 40 is preferably provided with a radio-opaque and/or echo-opaque portion 44 which is located at the distal end 46 with such a length as to allow the display of the folding thereof when it is withdrawn inside the first catheter 30 by the snaring member 20. This radio-opaque and/or echo-opaque portion 44 simplifies the above-described operation of advance of the second catheter 40 until having the distal end 46 near the at least one loop of the snaring member when this operation is carried out inside a patient, with a display by means of echography and/or radioscopy. Similarly, the presence of the radio-opaque and/or echo-opaque portion 44 allows verification that the second catheter 40 does not leave the loops 22 of the snaring member 20 when the end portion 52 of the guide wire is withdrawn. In other words, it serves to verify that, between the step of FIG. 3 and that of FIG. 4, the catheter remains positioned in the correct manner.

At the same time, by having a predominant portion 42 of the second catheter 40 which is radio-transparent and/or echo-transparent, it is possible to position the end of the guide wire 50 outside the portion of the second catheter 40 which is caught by the loops 22 of the snaring member, preserving the integrity thereof. In fact, the guide wire is normally radio-opaque and echo-opaque, usually being made of metal, and therefore is clearly visible when it is in the echo-transparent and/or radio-transparent portion of the second catheter 40.

From what has been described above, it is evident that, if it is desirable to draw the second catheter 40 inside the first catheter 30, the first catheter 30 of the snaring device has such an internal diameter as to allow the passage of the second catheter 40 which is folded on itself, with play. If it is desirable to simply capture the second catheter 40 between the snaring member and the end hole 32 of the first catheter 30, however, it is not necessary for the first catheter 30 to be able to accommodate the second catheter therein. Neither is it excluded that the first catheter 30 may have a lumen with a diameter less than the second catheter 40.

In the description of the method set out above, it is considered that the second catheter 40 is inserted once the guide wire has already been arranged correctly, simply causing the second catheter to slide over the guide wire. If this were not possible or convenient, it is in any case possible to arrange the guide wire 50 inside the second catheter 40 before the use thereof.

During the advance operation of the second catheter 40 on the guide wire 50, it may be necessary to take care not to lose the correct positioning of the guide wire. To this end, it may be advantageous once the guide wire is in the position of FIG. 2, that is to say, with the end portion 52 thereof which crosses at least one loop 22 of the snaring member 20, to withdraw the snaring member 20 inside the first catheter 30 but without capturing the loops 22. In this manner, the distal end of the guide wire becomes stabilized without it becoming damaged, maintaining it correctly positioned while the second catheter 40 is caused to slide over it.

It may then be noted that the above description always makes reference to a device for capturing a single guide wire 50 which is accommodated in a second catheter 40. However, it will be understood that it may also be used for capturing more than one guide wire. In this case, it is simply necessary to provide an additional catheter 40, with the same characteristics described above, for each of the additional guide wires provided.

The second catheter may be constructed by joining various portions which are constructed, some from uncharged polymer material for the echo-transparent/radio-transparent portions and others from polymer material which is charged with suitable additives, for example, barium sulphate (BaSO4), for the radio-opaque portions. It may further be advantageous to use polymers with a relative greater hardness and rigidity for the main portions of the second catheter so as to be suitable for overcoming the possible resistances to advancing, while the distal end 46 which is intended to be caught and folded by the snaring device is advantageously constructed from polymer materials with little hardness and with greater flexibility so as to be suitable for being deformed for the stability of the capture without any risks of breakage or damage.

Naturally, the principle of the invention remaining the same, the forms of embodiment and details of construction may be varied widely with respect to those described and illustrated, without thereby departing from the scope of the invention.

The invention claimed is:

1. A device for capturing a guide wire having a distal end, the device comprising:

a snaring device; and an auxiliary catheter having a distal end and an end hole, the auxiliary catheter being configured to slidingly accommodate the guide wire to be caught so as to extend the distal end of the auxiliary catheter beyond the distal end of the guide wire in order to be caught by the sharing device while the guide wire is in a retracted position in the auxiliary catheter, wherein the auxiliary catheter is at least partially echo-transparent and/or radio-transparent over at least a portion thereof and includes a radio-opaque and/or echo-opaque portion near the end hole.

2. The device according to claim 1, wherein the at least partially echo-transparent and/or radio-transparent portion of the auxiliary catheter is predominant.

3. The device according to claim 1, wherein the sharing device includes a first catheter and the radio-opaque and/or echo-opaque portion has a length sufficient for display in a folded form during introduction of the auxiliary catheter into the first catheter of the snaring device.

4. The device according to claim 1, wherein the sharing device comprises a snaring member and a rod, the snaring member comprising at least one loop mounted on the rod.

5. The device according to claim 1, wherein the auxiliary catheter has an internal diameter configured to allow insertion and sliding of a single guide wire.

6. The device according to claim 1, wherein the auxiliary catheter is constructed from polymer material.

7. A method for capturing a guide wire, comprising the steps of:

providing the device for capturing the guide wire having the distal end according to claim 1;

positioning the guide wire in a desired position;

positioning the snaring device so that the distal end of the guide wire engages with the sharing device or crosses the sharing device;

arranging the auxiliary catheter over the guide wire;

sliding the auxiliary catheter along the guide wire so that the auxiliary catheter crosses or engages with the sharing device;

withdrawing the guide wire such that an end thereof does not cross or engage with the sharing device; and withdrawing a snaring member of the snaring device inside a catheter, thereby capturing the auxiliary catheter.

8. The method according to claim 7, further including folding the at least partially echo-transparent and/or radio-transparent portion of the auxiliary catheter when the sharing member captures the auxiliary catheter, thereby indicating visually, by echographic and/or radiographic images, the correct capture of the auxiliary catheter by the snaring device.

* * * * *